June 18, 1940.
E. A. BRIGGS
GLADIOLUS
Filed Feb. 27, 1939
Plant Pat. 404
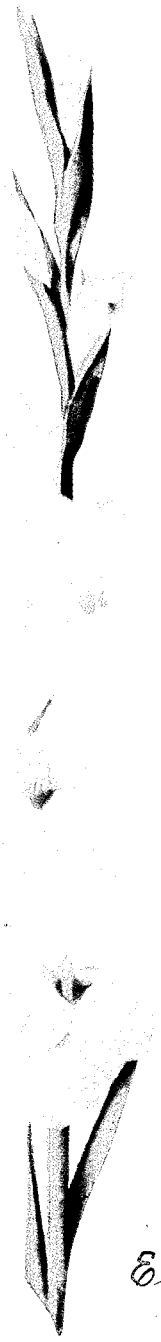
*Inventor*
Elizabeth A. Briggs Patented June 18, 1940

Plant Pat. 404

UNITED STATES PATENT OFFICE

404

GLADIOLUS

Elizabeth A. Briggs, Encinitas, Calif., assignor to Chas. E. Ogg, Encinitas, Calif.

Application February 27, 1939, Serial No. 258,738

1 Claim. (Cl. 47—60)

My present invention relates to improvements in flowering gladioli of the type notable for earliness of bloom and hardiness in growth out of doors in the winter and the propensity to prolific bloom, and for its clarity of color and lasting qualities of bloom. The object of this invention is to provide a gladiolus of superior Rose Doree color with pure white blotch in the throat, with large individual flowers of excellent substance and well placed and well formed.

My new variety of gladiolus originated as a seedling produced from cross pollination work carried on by myself. To the best of my knowledge and belief the parents of this new variety were the variety "Bridesmaid" and an unnamed pink variety produced by myself. It first bloomed in May, 1933. "Bridesmaids" was the result of a cross of W. H. Phipps (parents unknown) on a pink unnamed seedling of my own origination. The unnamed pink seedling was the result of a hand pollinated cross by the applicant between two unnamed seedlings. This applicant takes no precaution to prevent admixture of pollen by wind or insects in making her crosses.

The accompanying illustration shows in reduced size a freshely cut spike of my new variety, as true to nature as the artist could paint it. It must be understood, however, that the painting cannot depict the softness of the coloring of the natural flower.

Following is a more complete description of the plant and flower of this new variety.

*The plant*

The plant is a very vigorous grower and the tips of the spikes usually reach a height of 48 inches above the ground. Foliage is very dark green and exceptionally broad and vigorous. Color of the foliage is Deep Dull Yellow Green (2) (Plate XXXII Ridgway's Color Standards and Nomenclature).

This variety is more vigorous and a hardier grower in winter and an earlier bloomer than similar varieties of Rose Doree gladioli grown under the same conditions of soil and climate. Usually each spike opens five to seven of its clear colored flowers at one time and has a total of seventeen to twenty flowers in all.

Corm is firm, healthy and not subject to disease. Color of corm is Wax Yellow (Plate XVI Ridgway's Color Standards and Nomenclature). Corm is covered to root scar with a heavy tunic Light Vinaceous Cinnamon in color (Plate XXIX Ridgway's Color Standards and Nomenclature).

*The spike and flower*

The individual flowers are large, the lower blossoms usually being four and one-half to five and one-half inches in diameter.

These flowers consist of six petals of uniform size and shape. The petals are smooth and unwrinkled, and have a smooth clear color with unnotched and unwrinkled edges. They are of heavy substance thus making the variety very valuable for shipping and long keeping.

Three white stamens arise from the center of the throat and are topped with anthers containing much pollen and are of Pale Hortense Violet color (Plate XI Ridgway's Color Standards and Nomenclature). Arising from the center of the stamens is a single slender, white style which terminates in three short spreading branches.

The calyx is Deep Dull Yellow Green in color (2) (Plate XXXII Ridgway's Color Standards and Nomenclature) and is firmly attached to the flower.

The flower stalk is stiff and vigorous and is Deep Dull Yellow Green in color (2) (Plate XXXII Ridgway's Color Standards and Nomenclature).

The color in Ridgway's Color Standards and Nomenclature which most nearly approaches the color of this new variety is clear Rose Doree (Plate I). The throat is marked with a pure white blotch.

Other known varieties of somewhat similar coloring have not the clarity and smoothness of color. Rose Doree varieties somewhat similar are Frank J. McCoy and Giant Nymph.

The most notable characteristics which readily distinguish my new gladiolus from all other known Rose Doree varieties and particularly from Frank J. McCoy and Giant Nymph, are:

1. The smoothness and clarity of color.
2. The earliness of bloom.
3. The hardiness in growth when grown out of doors in the winter.
4. The unusually good shipping and keeping qualities.
5. The propensity to prolific bloom.

Having thus disclosed my invention, I claim:

The new variety of gladiolus plant herein described and illustrated, characterized particularly by its earliness of bloom, hardiness in growth out of doors in the winter, smoothness and clarity of color, unusually good shipping and keeping qualities and propensity to prolific bloom, as described.

ELIZABETH A. BRIGGS.